United States Patent [19]

Midgley et al.

[11] Patent Number: 5,102,486

[45] Date of Patent: Apr. 7, 1992

[54] LOOP APPLYING ASSEMBLY

[75] Inventors: Roland R. Midgley, Minneapolis; Donald L. Plaschko, Woodbury, both of Minn.

[73] Assignee: Minnesota Mining and Manufacturing Company, St. Paul, Minn.

[21] Appl. No.: 639,193

[22] Filed: Jan. 9, 1991

[51] Int. Cl.⁵ .......................................... B32B 31/00
[52] U.S. Cl. ................................. 156/256; 156/292; 156/302; 156/443; 156/494; 156/519; 156/553
[58] Field of Search .............. 156/302, 256, 146, 292, 156/443, 494, 495, 519, 553, 70, 162, 164

[56] References Cited

U.S. PATENT DOCUMENTS

| | | | |
|---|---|---|---|
| 2,582,165 | 1/1952 | Rosenfeld | 26/51 |
| 2,702,406 | 2/1955 | Reed | 26/72 |
| 3,728,191 | 2/1974 | Wierzba et al. | 156/302 |
| 3,750,511 | 8/1973 | Toensing | 83/337 |
| 3,960,646 | 6/1976 | Wiedamann | 156/518 |
| 4,001,072 | 1/1977 | deNeul | 156/461 |
| 4,171,239 | 10/1980 | Hirsch et al. | 156/519 |
| 4,284,454 | 3/1981 | Joa | 156/519 |
| 4,285,747 | 3/1981 | Rega | 156/302 |
| 4,642,150 | 2/1987 | Stemmler | 156/164 |
| 4,925,520 | 5/1990 | Beaudoin et al. | 156/494 |
| 4,943,340 | 1/1989 | Ujimoto et al. | 156/302 |

Primary Examiner—W. Gary Jones
Assistant Examiner—David Reifsnyder
Attorney, Agent, or Firm—Gary L. Griswold; Walter N. Kirn; William L. Huebsch

[57] ABSTRACT

A method for applying loops formed from a supply length of elongate strip material in spaced relationship along a substrate. Lengths are cut from the supply length, and have their ends supported on peripheral surfaces of two circular disks mounted with their axes oriented to position portions of the peripheral surfaces of the disks on which the lengths are positioned at a wide spacing at a first location and to position portions of the peripheral surfaces of the disks at a close spacing significantly closer than the wide spacing at a second location generally diametrically across the disks from the first location and along a path for the substrate. Spaced portions of the lengths are held along the peripheral surfaces of the disks during rotation of the disks to move the predetermined lengths from the first location to the second location thereby forming the lengths into generally U-shaped loops, and those U-shaped loops are transferred and attached to the substrate at the second location.

12 Claims, 4 Drawing Sheets

LOOP APPLYING ASSEMBLY

TECHNICAL FIELD

The present invention relates to devices and methods for applying loops of material in spaced relationship on a substrate, and in one important aspect, to devices and methods for applying loops around an edge of a substrate with end portions of the loops attached to opposite sides of the substrate.

BACKGROUND ART

Assemblies are known that apply, in spaced relationship along a substrate, lengths of a supply length of elongate strip material. Such assemblies are described in U.S. Pat. Nos. 3,750,511; 3,960,646; and 4,001,072. Such assemblies typically include means defining a substrate path for the substrate relative to a frame; means for moving the substrate at a first rate of speed along the substrate path; means defining a supply path relative to the frame and terminating adjacent the substrate path for guiding the supply length of elongate strip material; means for moving the supply length of elongate strip material along the supply path at a second rate of speed that is slower than the first rate of speed; cutting means for cutting predetermined lengths from the supply length of elongate strip material; and applying means for applying the cut lengths of the elongate strip material in spaced relationship along the substrate. While in applying closure tabs to disposable diapers such lengths have been applied with parts projecting past an edge of the substrate, and the projecting parts have subsequently been folded around an edge of the substrate, such application requires very good web edge control and occasionally leads to the tabs being folded askew or in a wrinkled condition. Thus this method is not very satisfactory when used to apply such cut lengths in a loop around the edge of a very thin, flexible web or substrate as is required to make the polymeric trash bags described in U.S. Pat. application Ser. No. 560,430 filed July 31, 1990, which is assigned to the assignee of this application, the content whereof is incorporated herein by reference.

DISCLOSURE OF INVENTION

The present invention provides an assembly and method for applying, in spaced relationship along a substrate, lengths of a supply length of elongate strip material having opposite edges and a predetermined width between the edges with portions of each applied length adjacent the edges attached to the substrate in closely spaced relationship to form a loop from the applied length, which assembly and method can be adapted to apply the lengths with portions of each applied length adjacent the edges attached to opposite sides of the substrate and the loop extending around an edge of the substrate, as is useful to apply such lengths in a loop around the edge of a disposable diaper to provide a fastener portion, or to apply such lengths in a loop around the edge of a very thin, flexible web to provide the structure described in U.S Pat. application Ser. No. 560,430.

The assembly according to the present invention includes means defining a substrate path for the substrate relative to the frame; means for moving the substrate at a first rate of speed along the substrate path; means defining a supply path relative to the frame and terminating adjacent the substrate path for guiding the supply length of elongate strip material; means for moving the supply length of elongate strip material along the supply path at a second rate of speed that is slower than the first rate of speed; cutting means for cutting predetermined lengths from the supply length of elongate strip material; and applying means for applying the cut lengths of the elongate strip material in spaced relationship along the substrate with portions of each applied length adjacent the edges attached to the substrate in closely spaced relationship to form a loop from the applied length. The applying means comprises two circular disks each having an axis and a peripheral surface around the axis; means mounting the disks on the frame for rotation about the axes with the axes being oriented to position portions of the peripheral surfaces of the disks at a wide spacing at a first location relative to the frame adjacent the cutting means, and to position portions of the peripheral surfaces of the disks at a close spacing significantly closer than the side spacing at a second location relative to the frame generally diametrically across the disks from the first location and along the substrate path; means for rotating the disks to move the peripheral surfaces of the disks from the first location to the second location; and means for transferring the predetermined lengths from the cutting means to the peripheral surfaces of the disks adjacent the first location; for holding portions of the predetermined lengths along the peripheral surfaces of the disks during rotation of the disks to move the predetermined lengths from the first location to the second location, and means at the second location for transferring and attaching portions of the applied lengths to the substrate.

As illustrated herein, the assembly is adapted to apply the lengths with portions of each applied length adjacent the edges attached to opposite sides of the substrate and the loop extending around an edge of the substrate in that the means defining a substrate path for the substrate relative to the frame and the means for moving the substrate at a first rate of speed along the substrate path positions and moves a portion of the substrate between the disks at the second location with each of the opposite sides of the substrate adjacent a different one of the peripheral surfaces of the disks.

BRIEF DESCRIPTION OF DRAWING

The present invention will be further described with reference to the accompanying drawing wherein like reference numerals refer to like parts in the several views, and wherein.

DETAILED DESCRIPTION

Figures 1, 2:
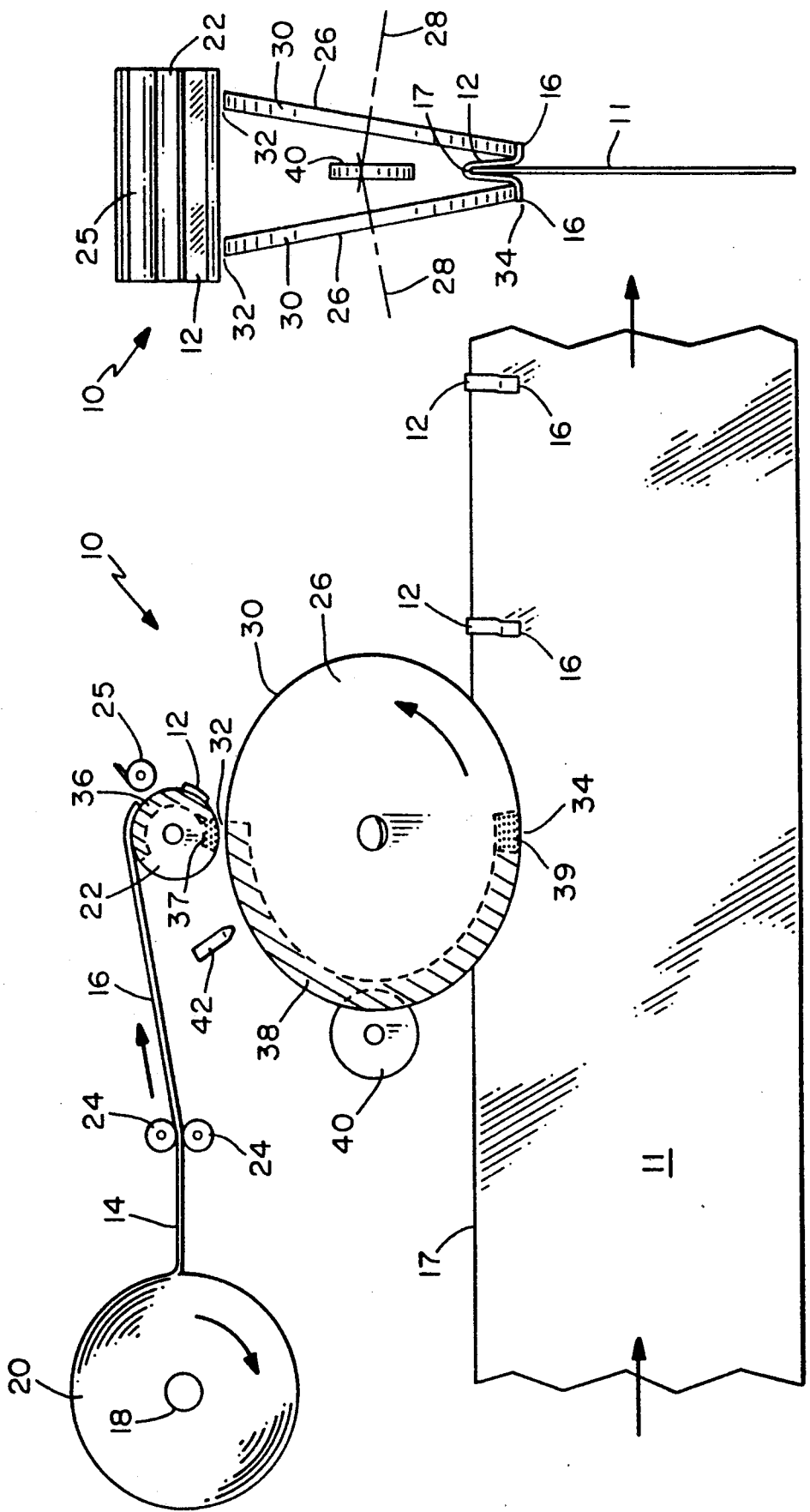
FIG. 1 is a schematic vertical side view of a first embodiment of an assembly according to the present invention.
FIG. 2 is a vertical end view of the assembly of FIG. 1.

Referring now to FIGS. 1 and 2 of the drawing, there is schematically shown an assembly 10 according to the present invention for applying, in spaced relationship along a substrate 11, lengths 12 of a supply length 14 of elongate strip material having opposite edges 16 and a predetermined width between the edges 16 with portions of each applied length 12 adjacent the edges 16 attached to the substrate 11 in closely spaced relationship to form a loop from the applied length 12, which assembly 10 is adapted to apply the lengths 12 with portions of each applied length 12 adjacent the edges 16 attached to opposite sides of the substrate 11 and the loop extending around an edge 17 of the substrate 11.

Generally the assembly 10 includes means (not shown) defining a substrate path for the substrate 11 relative to the frame; means (also not shown) for moving the substrate 11 at a first rate of speed along the substrate path; means defining a supply path relative to the frame and terminating adjacent the substrate path for guiding the supply length 14 of elongate strip material including a hub 18 for supporting a roll 20 of the elongate strip and a vacuum roller 22; means for moving the supply length 14 of elongate strip material along the supply path at a second rate of speed that is slower than the first rate of speed provided by a driven pair of drive rollers 24; cutting means including a rotated cutter 25 for cutting predetermined lengths from the supply length 14 of elongate strip material against the cylindrical peripheral surface of the vacuum roller 22; and applying means including the vacuum roller 22 and two circular disks 26 for applying the cut lengths 12 of the elongate strip in spaced relationship along the substrate 11 with portions of each applied length 12 adjacent the edges 16 attached to the substrate 11 in closely spaced relationship to form a loop from the applied length 12. The two circular disks 26 are mounted on the frame for rotation about their axes 28 with their axes 28 being oriented (as is best seen in FIG. 2) to position portions of peripheral surfaces 30 of the disks 26 at a wide spacing at a first location 32 relative to the frame adjacent the cutting means, and to position portions of the peripheral surfaces 30 of the disks 26 at a close spacing significantly closer than the side spacing at a second location 34 relative to the frame generally diametrically across the disks 26 from the first location 32 and along the substrate path. Means are provided for rotating the disks 26 to move the peripheral surfaces 30 of the disks 26 from the first location 32 to the second location 34 at a peripheral speed about the same as the linear speed the substrate 11 is moved along its path; as are means for transferring the predetermined lengths 12 from the cutting means to the peripheral surfaces 30 of the disks 26 adjacent the first location 32; for holding end portions of the predetermined lengths 12 along the peripheral surfaces 30 of the disks 26 during rotation of the disks 26 to move the predetermined lengths 12 from the first location 32 to the second location 34 so that the predetermined lengths 12 change from being straight to having a U or loop-like shape as the portions of the peripheral surfaces 30 along which end portions of the predetermined lengths 12 are held move closer together, and means at the second location 34 for transferring and attaching portions of the U or loop-like shaped lengths 12 to the substrate 11.

The means for transferring the predetermined lengths 12 from the cutting means to the peripheral surfaces 30 of the disks 26 adjacent the first location 32; for holding end portions of the predetermined lengths 12 along the peripheral surfaces 30 of the disks 26 during rotation of the disks 26 to move the predetermined lengths 12 from the first location 32 to the second location 34, and the means at the second location 34 for transferring and attaching portions of the U or loop-like shaped lengths 12 to the substrate 11 are provided by openings through the cylindrical periphery of the vacuum roller 22 and openings through the cylindrical peripheral surfaces of the disks 26; a manifold connected to a source of low pressure air or vacuum which communicates through the openings in the peripheral surface of the vacuum roller 22 in an arc 36 indicated by cross hatching from the approximate position the supply length 14 of elongate strip first contacts that peripheral surface to a position just before the area in which the peripheral surfaces of the vacuum roller 22 and the disks 26 are closest to each other; a manifold connected to a source of high pressure air which communicates through the openings in the peripheral surface of the vacuum roller 22 in an area 37 indicated by stippling at which the vacuum roller 22 and the disks 26 are closest to each other, manifolds connected to the source of low pressure air or vacuum which communicate through the openings in the peripheral surfaces of the disks 26 in an arc 38 indicated by cross hatching extending in the direction of travel of the disks 26 from the first location 32 at which the peripheral surfaces 30 of the disks 26 are closest to the vacuum roller 22 to a position just before the second location 34, and a manifold connected to the source of high pressure air which communicates through the openings in the peripheral surfaces of the disks 26 in an area 39 indicated by stippling at the second location 34. The vacuum applied along the arc 36 holds the end of the supply length 14 of elongate strip material along the peripheral surface of the vacuum roller 22 and applies a force tending to advance that end along that peripheral surface which rotates faster than the rate of advancement of the supply length 14 so that the end of the supply length 14 slips relative to it. When one of the predetermined lengths 12 is cut from the end of the supply length 14 by the cutter 25, that predetermined length 12 will be held along and advanced at the same rate as the peripheral surface of the vacuum roller 22 until it reaches the area 37 where the vacuum holding is terminated and the air pressure presses the end portions of the length 12 against the peripheral surfaces 30 of the disks 26. The vacuum applied along the arc 38 will then hold the end portions of the length 12 on those moving peripheral surfaces 30 until the length 12 reaches the area 39 where the vacuum holding is terminated. The peripheral surfaces 30 of the disks 26 can be spaced and shaped to press the portions of the lengths 12 supported on them against the substrate 11 at the second location 34, which pressing can be added to by air pressure through the periphery of the disk at the area 39 if needed or desired.

The assembly 10 is adapted to apply the lengths 12 with portions of each applied length 12 adjacent the edges 16 attached to opposite sides of the substrate 11 and the loop extending around the edge 17 of the substrate 11 in that the means defining a path for the substrate 11 relative to the frame and the means for moving the substrate 11 at a first rate of speed along the substrate path positions and moves a portion of the substrate 11 between the disks 26 at the second location 34 with each of the opposite sides of the substrate 11 adjacent a different one of the peripheral surfaces 30 of the disks 26. Alternatively, the assembly could apply the lengths 12 in spaced relationship along one surface of a substrate generally tangent to the peripheral surfaces of both disks 26 at the second location.

The assembly 10 further includes means in the form of a circular guide member 40 rotatably mounted on the frame between the peripheral surfaces 30 of the disks 26 and between the first and second locations 32 and 34 positioned for guiding central portions of the lengths 12 so that the lengths have U or loop-like shapes in a predetermined orientation projecting radially inwardly of the disks 26 from the peripheral surfaces 30 of the disks 26.

Also, the assembly 10 includes means including two adhesive applying nozzles 42 for applying two coatings of adhesive along one surface of the lengths 12, one coating adjacent each opposite edge 16, which adhesive could be a hot melt pressure sensitive adhesive, or a thermoplastic adhesive. Means are provided for only expelling adhesive from the nozzles when the lengths 12 pass the nozzles 42. The peripheral surfaces 30 of the disks 26 can be spaced and shaped to press the portions of the lengths 12 supported on their peripheries 30 against the substrate 11 at the second location 34 to adhere the adhesive to the substrate 11, which pressing can be added to by air pressure through the periphery of the disk at the area 39 if needed.

Figure 3:
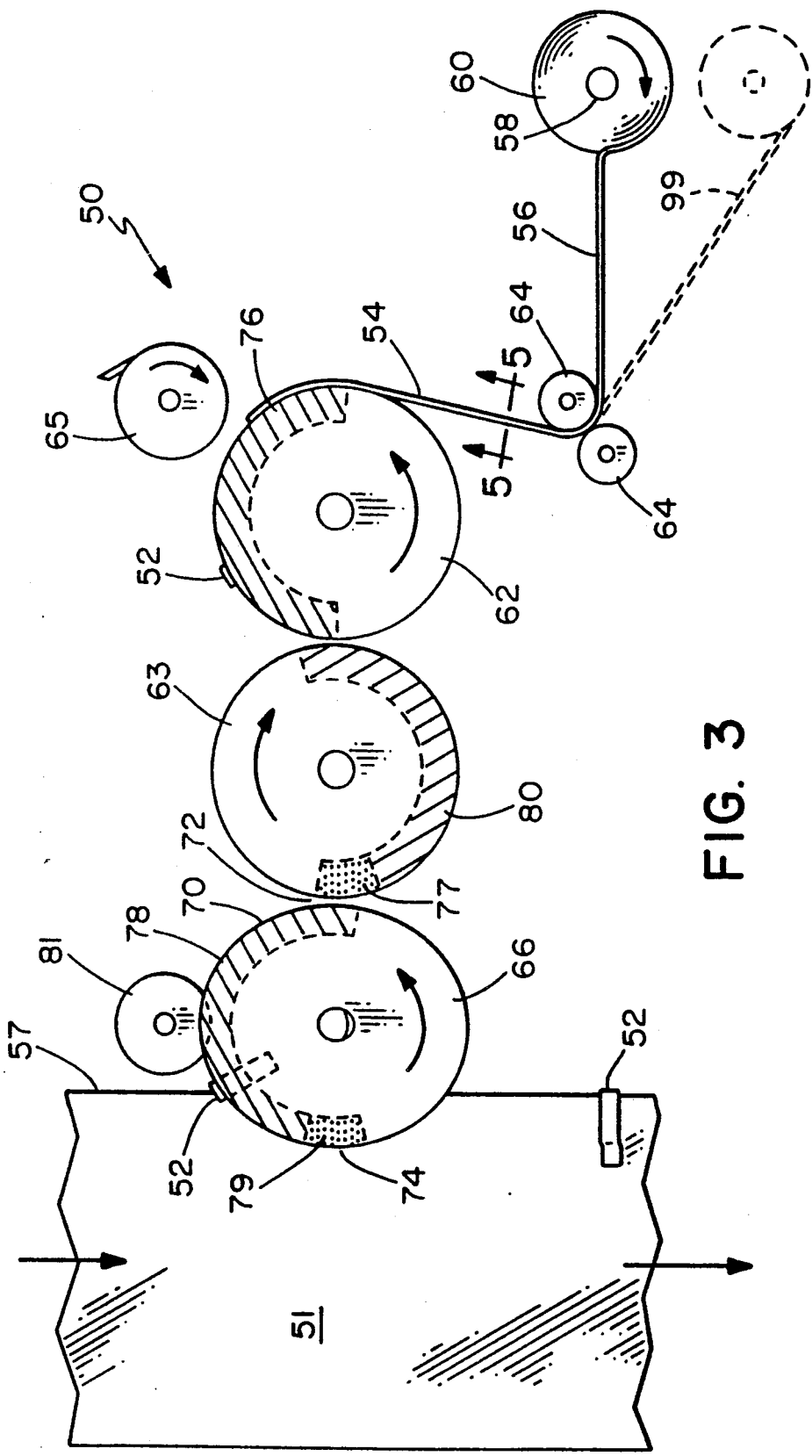
FIG. 3 is a schematic vertical side view of a second embodiment of an assembly according to the present invention.
Figure 4:
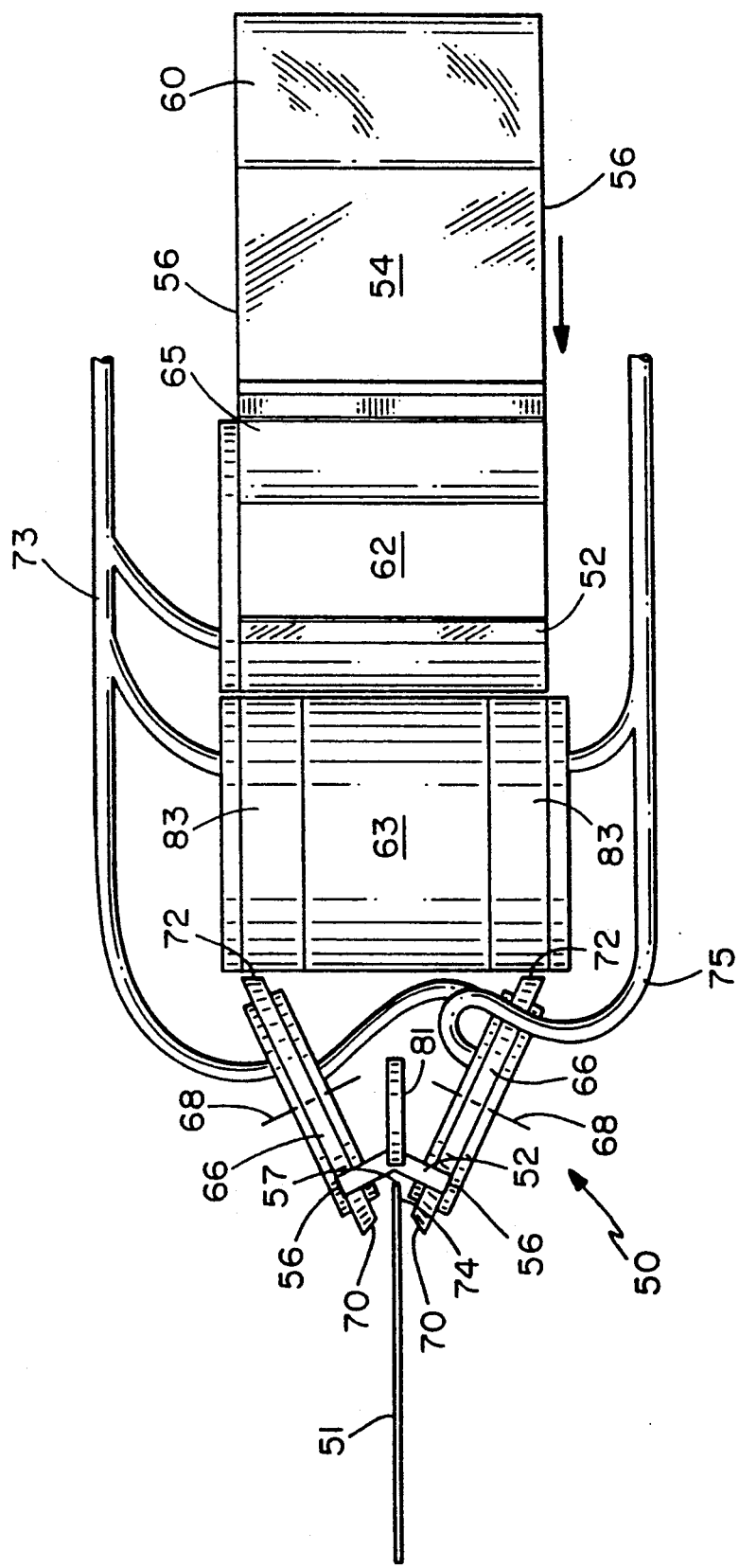
FIG. 4 is a top view of the assembly of FIG. 3.

Referring now to FIGS. 3 and 4 of the drawing, there is schematically shown an assembly 50 according to the present invention for applying, in spaced relationship along a substrate 51, lengths 52 of a supply length 54 of elongate strip material having opposite edges 56 and a predetermined width between the edges 56 with portions of each applied length 52 adjacent the edges 56 attached to the substrate 51 in closely spaced relationship to form a loop from the applied length 52, which assembly 50 is adapted to apply the lengths 52 with portions of each applied length 52 adjacent the edges 56 attached to opposite sides of the substrate 51 and the loop extending around an edge 57 of the substrate 51.

Generally the assembly 50 includes means (not shown) defining a substrate path for the substrate 51 relative to the frame; means (also not shown) for moving the substrate 51 at a first rate of speed along the substrate path; means defining a supply path relative to the frame and terminating adjacent the substrate path for guiding the supply length 54 of elongate strip material including a hub 58 for supporting a roll 60 of the elongate strip and a first vacuum roller 62; means for moving the supply length 54 of elongate strip material along the supply path at a second rate of speed that is slower than the first rate of speed provided by a driven pair of drive rollers 64; cutting means including a rotated cutter 65 for cutting predetermined lengths from the supply length 54 of elongate strip material along the peripheral surface of the first vacuum roller 62; and applying means including the first vacuum roller 62, a second vacuum roller 63, and two circular disks 66 for applying the cut lengths 52 of the elongate strip in spaced relationship along the substrate 51 with portions of each applied length 52 adjacent the edges 56 attached to the substrate 51 in closely spaced relationship to form a loop from the applied length 52. The two circular disks 66 in the applying means each have an axis 68 and a peripheral surface 70 around the axis 68. The disks 66 are mounted on the frame for rotation about their axes 68 with their axes 68 being oriented (as is best seen in FIG. 4) to position portions of the peripheral surfaces 70 of the disks 66 at a wide spacing at a first location 72 relative to the frame adjacent the cutting means and second vacuum roller 63, and to position portions of the peripheral surfaces 70 of the disks 66 at a close spacing significantly closer than the wide spacing at a second location 74 relative to the frame generally diametrically across the disks 66 from the first location 72 and along the substrate path. Means are provided for rotating the disks 66 to move the peripheral surfaces 70 of the disks 66 from the first location 72 to the second location 74 at a peripheral speed about the same as the linear speed the substrate 51 is moved along its path; as are means for transferring the predetermined lengths 52 from the cutting means to the peripheral surfaces 70 of the disks 66 adjacent the first location 72; for holding end portions of the predetermined lengths 52 along the peripheral surfaces 70 of the disks 66 during rotation of the disks 66 to move the predetermined lengths 52 from the first location 72 to the second location 74 so that the predetermined lengths 52 change from being straight to having a U or loop-like shape as the portions of the peripheral surfaces 70 along which end portions of the predetermined lengths 52 are held move closer together; and means at the second location 74 for transferring and attaching portions of the U or loop-like shaped lengths 52 to the substrate 51.

The means for transferring the predetermined lengths 52 from the cutting means to the peripheral surfaces 70 of the disks 66 adjacent the first location 72; for holding end portions of the predetermined lengths 52 along the peripheral surfaces 70 of the disks 66 during rotation of the disks 66 to move the predetermined lengths 52 from the first location 72 to the second location 74, and the means at the second location 74 for transferring and attaching portions of the applied lengths 52 to the substrate 51 are provided by openings through the cylindrical peripheral surfaces of the first and second vacuum rollers 62 and 63, openings through the cylindrical peripheral surfaces 70 of the disks 66, a manifold 73 connected to a source of low pressure air or vacuum which communicates through the openings in the peripheral surfaces of the vacuum rollers 62 and 63 in arcs 76 and 80 indicated by cross hatching, with the arc 76 extending from the approximate location the end of the supply length 54 of elongate strip first contacts the peripheral surface of the first vacuum roller 62 to a location at which the peripheral surfaces of the first and second vacuum rollers 62 and 63 are closest, and the arc 80 extending from the location at which the peripheral surfaces of the first and second vacuum rollers 62 and 63 are closest to just before the location at which the peripheral surfaces of the second vacuum roller 63 and the disks 66 are closest to each other; and a manifold 75 connected to a source of high pressure air which communicates through the openings in the peripheral surface of the second vacuum roller 63 in an area 77 indicated by stippling at which the peripheral surfaces of the second vacuum roller 63 and the disks 66 are closest to each other. The manifold 73 connected to the source of low pressure air also communicate through the openings in the peripheral surfaces 70 of the disks 66 in arcs 78 indicated by cross hatching extending in the direction of travel of the disks 66 from the first location 72 at which the peripheral surfaces 70 of the disks 66 are closest to the peripheral surface of the second vacuum roller 63 to a position just before the second location 74, and the manifold 75 is connected to the source of high pressure air which communicates through the openings in the peripheral surfaces 70 of the disks 66 in areas 79 indicated by stippling at the second location 74. The vacuum applied along the arc 76 holds the end of the supply length 54 of elongate strip material along the peripheral surface of the vacuum roller 62 and applies a force tending to advance that end along that peripheral surface which rotates faster than the rate of advancement of the supply length 54 so that the end of the supply length 54 slips relative to it. When one of the predetermined lengths 52 is cut from that end by the cutter 65, it will be held along and advanced at the same rate as the peripheral surface of the first vacuum roller 62 until it reaches the end of the arc 76 at which it will be transferred to the peripheral surface 83 of the second vacuum roller 63 under the influence of vacuum acting in the arc 80. The length 52 will then be held along and advanced at the same rate as the peripheral surface 83 of the second vacuum roller 63 until it reaches the area 77 at which the vacuum holding is terminated and the air pressure presses the ends of the length 52 against the peripheral surfaces 70 of the disks 66 so that the vacuum applied along the arcs 78 will then hold the ends of the length 52 on those peripheral surfaces 70 until the length 52 reaches the area 79, at which the vacuum holding is terminated and the shape and close spacing of the peripheral surfaces 70 of the disks 66 supplemented (if needed or desired) by air pressure applied through the peripheral surfaces 70 of the disks 66 in the area 79 presses the ends of the length 52 against the opposite sides of the substrate 51.

The assembly 50 is adapted to apply the lengths 52 with portions of each applied length 52 adjacent the edges 56 attached to opposite sides of the substrate 51 and the loop extending around the edge 57 of the substrate 51 in that the means defining a path for the substrate 51 relative to the frame and the means for moving the substrate 51 at a first rate of speed along the substrate path positions and moves a portion of the substrate 51 between the disks 66 at the second location 74 with each of the opposite sides of the substrate 51 adjacent a different one of the peripheral surfaces 70 of the disks 66. Alternatively, the assembly 50 could apply the lengths 52 in spaced relationship along one surface of a substrate generally tangent to the peripheral surfaces of both disks 66 at the second location 74.

The assembly 50 further includes means in the form of a circular guide member 81 rotatably mounted on the frame between the peripheral surfaces 70 of the disks 66 and between the first and second locations 72 and 74 positioned for guiding central portions of the lengths 52 so that the lengths 52 have U or loop-like shapes in a predetermined orientation projecting radially inwardly of the disks 66 from the peripheral surfaces 30 of the disks 66.

The assembly 50 is adapted for applying lengths of the supply length 54 having coatings or layers of thermoplastic or pressure sensitive adhesive adjacent its opposite edges facing away from the peripheral surface of the first vacuum roller 62 in that the peripheral surface of the second vacuum roller 63 has portions roughened or removed such as by knurling, or formed by a rough material such as 80 grit sandpaper to restrict adhesion of the adhesive thereto and afford transfer of the lengths 52 from the second vacuum roller 63 to the peripheral surfaces 66 of the disks 66. Alternatively, the second vacuum roller 63 may be replaced by a transfer roller that relies only upon adhesion between the layers of pressure sensitive adhesive and the peripheral surface of the transfer roller (which may be roughened as needed) to transfer the lengths 12 from the first vacuum roller 62 to the disks 66. Means for heating thermoplastic adhesive could also be incorporated in or along the peripheral surface of the second vacuum roller 63. The peripheral surfaces 70 of the disks 66 can be spaced and shaped to press the portions of the lengths 52 supported on their peripheries 70 against the substrate 51 at the second location 74 to adhere the adhesive to the substrate 51, which pressing can be added to by air pressure through the periphery of the disk at the area 79 if needed.

Figure 5:
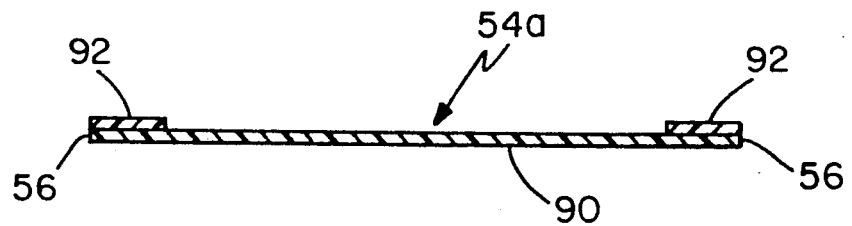
FIGS. 5, 6 and 7 are cross sectional views taken approximately along line 5—5 of FIG. 3 illustrating two different structures of elongate strip material, cut lengths of which can be applied to a substrate by the assembly of FIG. 3.
Figure 6:
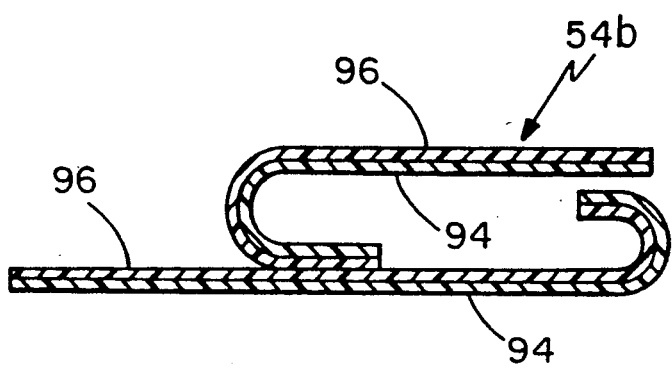
Figure 7:
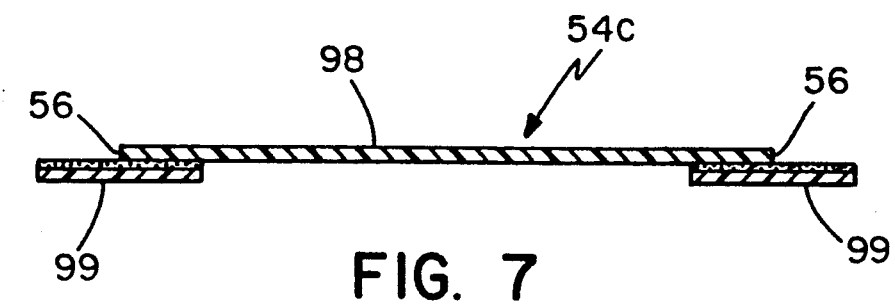

FIGS. 5, 6 and 7 illustrate three of many possible structures for the supply length 54 as viewed from line 5—5 of FIG. 3.

FIG. 5 illustrates a supply length 54a which comprises a main layer 90 which could be elastic or non elastic and of polymeric film material or woven or non woven fabric, and two layers 92 of thermoplastic or pressure sensitive adhesive along one surface adjacent the edges 56 of the supply length 54a. The main layer 90 and the two layers 92 of the supply length 54a can be pre-laminated and provided in the roll 60.

FIG. 6 illustrates a supply length 54b comprising two portions 94, each of which could be of polymeric film material or woven or non woven fabric, an edge part of on of the portions 94 being adhered along the center of the other and folded back, and the portions 94 being coated with layers 96 of thermoplastic or pressure sensitive adhesive. The structure of the supply length 54b is of a type that could be used to provide closures for disposable diapers, in which case the substrate 51 would be the main liquid absorbing portion for the disposable diapers, and a second assembly similar to the assembly 50 would be used to also attach closures along the edge of the substrate opposite the edge 57.

FIG. 7 illustrates a supply length 54c which comprises a main layer 98 which could be elastic or non elastic and of polymeric film material or woven or non woven fabric, and two lengths 99 of tape coated with pressure sensitive adhesive adhered along one surface of the main layer 98 with edge portions of the lengths 92 of tape projecting past the opposite edges of the main layer to define the edges 56 of the supply length 54c and expose pressure sensitive adhesive by which the lengths 12 can be adhered to the substrate 51. To provide the supply length 54c the assembly 50 can be modified as illustrated in dotted outline in FIG. 3 so that the main layer 98 is provided in the roll 60, and the two strips 99 of tape are laminated to the main layer 98 at the drive rollers 64.

The present invention has now been described with reference to two embodiments and several thereof. It will be apparent to those skilled in the art that many changes can be made in the embodiments described and the uses for those embodiments without departing from the scope of the present invention. Thus the scope of the present invention should not be limited to the structures described in this application, but only by structures described by the language of the claims and the equivalents of those structures.

I claim:

1. An assembly for applying, in spaced relationship along a substrate, lengths of a supply length of elongate strip material having opposite edges and a predetermined width between said edges with portions of each applied length adjacent said edges attached to the substrate in closely spaced relationship to form a loop from the applied length, said device comprising:

a frame;

means defining a substrate path for said substrate relative to said frame;

means for moving said substrate at a first rate of speed along said substrate path;

means defining a supply path relative to said frame and terminating adjacent said substrate path for guiding said supply length of elongate strip material;

means for moving said supply length of elongate strip material along said supply path at a second rate of speed that is slower than said first rate of speed;

cutting means for cutting predetermined lengths from the supply length of elongate strip material; and applying means for applying said cut lengths of the elongate strip material in spaced relationship along said substrate with portions of each applied length adjacent said edges attached to the substrate in closely spaced relationship to form a loop from the applied length, said applying means comprising:

two circular disks each having an axis and a peripheral surface around said axis;

means mounting said disks on said frame for rotation about said axes with said axes being oriented to position portions of the peripheral surfaces of the disks at a wide spacing at a first location relative to the frame adjacent said cutting means, and to position portions of the peripheral surfaces of the disks at a close spacing significantly closer than said side spacing at a second location relative to the frame generally diametrically across said disks from said first location and along said substrate path; means for rotating said disks to move the peripheral surfaces of said disks from said first location to said second location;

means for transferring the predetermined lengths from the cutting means to the peripheral surfaces of the disks adjacent said first location;

means for holding portions of the predetermined lengths along the peripheral surfaces of the disks during rotation of the disks to move the predetermined lengths from the first location to the second location; and means at said second location for transferring and attaching portions of the applied lengths to the substrate.

2. An assembly according to claim 1 adapted to apply the lengths with portions of each applied length adjacent said edges attached to opposite sides of the substrate and the loop extending around an edge of the substrate wherein said means defining a substrate path for said substrate relative to said frame and said means for moving said substrate at a first rate of speed along said substrate path positions and moves a portion of said substrate between said disks at said second location with each of the opposite sides of the substrate adjacent a different one of the peripheral surfaces of the disks.

3. An assembly according to claim 1 further including means fixed on said frame between the peripheral surfaces of said disks and between said first and second locations for guiding central portions of the lengths being applied to form the loops in a predetermined orientation relative to the peripheral surfaces of said disks.

4. An assembly according to claim 1 adapted for applying lengths of a supply length having coatings of pressure sensitive adhesive along said opposite edges wherein said peripheral surfaces of said disks are adapted to press the coatings of pressure sensitive adhesive against the substrate at said second location to provide said means at said second location for transferring and attaching portions of the applied lengths to the substrate.

5. An assembly according to claim 1 further including means for applying coatings of adhesive along one surface adjacent said opposite edges of the supply length and during movement of the supply length along said path, and said peripheral surfaces of said disks are adapted to press the coatings of adhesive against the substrate at said second location to provide said means at said second location for transferring and attaching portions of the applied lengths to the substrate.

6. An assembly according to claim 1 adapted for applying lengths of a supply length having layers of thermoplastic adhesive along said opposite edges wherein said assembly includes means for heating the layers of thermoplastic adhesive on the lengths and said peripheral surfaces of said disks are adapted to press the heated layers of thermoplastic adhesive against the substrate at said second location to provide said means at said second location for transferring and attaching portions of the applied lengths to the substrate.

7. A method for applying, in spaced relationship along a substrate, lengths of a supply length of elongate strip material having opposite edges and a predetermined width between the edges with portions of each applied length adjacent the edges attached to the substrate in closely spaced relationship to form a loop from the applied length, the method comprising the steps of:

providing means defining a substrate path for the substrate relative to a frame; means defining a supply path relative to the frame and terminating adjacent the substrate path for guiding the supply length of elongate strip material; cutting means for cutting predetermined lengths from the supply length of elongate strip material; and applying means for applying the cut lengths of the elongate strip material in spaced relationship along the substrate with portions of each applied length adjacent the edges attached to the substrate in closely spaced relationship to form a loop from the applied length, the applying means comprising two circular disks each having an axis and a peripheral surface around the axis, means mounting the disks on the frame for rotation about the axes with the axes being oriented to position portions of the peripheral surfaces of the disks at a wide spacing at a first location relative to the frame adjacent the cutting means and to position portions of the peripheral surfaces of the disks at a close spacing significantly closer than the side spacing at a second location relative to the frame generally diametrically across the disks from the first location and along the substrate path;

moving the substrate at a first rate of speed along the substrate path;

moving the supply length of elongate strip material along the supply path at a second rate of speed that is slower than the first rate of speed;

rotating the disks to move the peripheral surfaces of the disks from the first location to the second location;

transferring the predetermined lengths from the cutting means to the peripheral surfaces of the disks adjacent the first location; holding portions of the predetermined lengths along the peripheral surfaces of the disks during rotation of the disks to move the predetermined lengths from the first location to the second location; and transferring and attaching portions of the applied lengths to the substrate at the second location.

8. A method according to claim 7 adapted to apply the lengths with portions of each applied length adjacent the edges attached to opposite sides of the substrate and the loop extending around an edge of the substrate wherein said step of moving the substrate at a first rate of speed along the substrate path moves a portion of the substrate between the disks at the second location with each of the opposite sides of the substrate adjacent a different one of the peripheral surfaces of the disks.

9. A method according to claim 7 further including a step of guiding central portions of the lengths being applied between the first and second locations to form the loops in a predetermined orientation relative to the peripheral surfaces of the disks.

10. A method according to claim 7 adapted for applying lengths of a supply length having coatings of pressure sensitive adhesive adjacent the opposite edges wherein the method includes the step of pressing the coatings of adhesive against the substrate at the second location to provide said steps of transferring and attaching portions of the applied lengths to the substrate.

11. A method according to claim 7 further including steps of applying coatings of adhesive along one surface adjacent the opposite edges of the supply length during movement of the supply length along the path, and pressing the coatings of adhesive against the substrate at the second location with the peripheral surfaces of the disks to provide said steps of transferring and attaching portions of the applied lengths to the substrate at the second location.

12. A method according to claim 7 adapted for applying lengths of a supply length having layers of thermoplastic adhesive adjacent the opposite edges wherein the method includes the step of heating the layers of thermoplastic adhesive and pressing the heated layers of thermoplastic adhesive against the substrate at the second location to provide said steps of transferring and attaching portions of the applied lengths to the substrate.

* * * * *